(12) United States Patent
Banerjee

(10) Patent No.: US 11,103,545 B2
(45) Date of Patent: Aug. 31, 2021

(54) COMPOSITION FOR USE AS A MEDICINE OR DIETETIC FOOD IN THE PREVENTION AND/OR TREATMENT OF DIABETES AND DIABETES ASSOCIATED DISEASES

(71) Applicant: Shanta Banerjee, Berlin (DE)

(72) Inventor: Shanta Banerjee, Berlin (DE)

( * ) Notice: Subject to any disclaimer, the term of this patent is extended or adjusted under 35 U.S.C. 154(b) by 821 days.

(21) Appl. No.: 14/431,179

(22) PCT Filed: Sep. 27, 2013

(86) PCT No.: PCT/EP2013/070260
§ 371 (c)(1),
(2) Date: Mar. 25, 2015

(87) PCT Pub. No.: WO2014/049144
PCT Pub. Date: Apr. 3, 2014

(65) Prior Publication Data
US 2015/0238552 A1    Aug. 27, 2015

(30) Foreign Application Priority Data
Sep. 28, 2012 (EP) .................................... 12186698

(51) Int. Cl.
| | |
|---|---|
| *A61K 36/185* | (2006.01) |
| *A61K 36/87* | (2006.01) |
| *A61K 36/9066* | (2006.01) |
| *A61K 36/48* | (2006.01) |
| *A61K 36/47* | (2006.01) |
| *A61K 45/06* | (2006.01) |

(52) U.S. Cl.
CPC ............ *A61K 36/185* (2013.01); *A61K 36/47* (2013.01); *A61K 36/48* (2013.01); *A61K 36/87* (2013.01); *A61K 36/9066* (2013.01); *A61K 45/06* (2013.01)

(58) Field of Classification Search
CPC .... A61K 36/48; A61K 36/9066; A61K 36/87; A61K 36/185
USPC .................. 424/766, 776, 756, 777
See application file for complete search history.

(56) References Cited

U.S. PATENT DOCUMENTS

| | | | |
|---|---|---|---|
| 7,014,872 B2 | 3/2006 | Pushpangadan et al. | |
| 9,045,038 B2 * | 6/2015 | Walter | ............. B60K 15/03504 |
| 2005/0239887 A1 * | 10/2005 | Ochoa | .................. A61K 31/155 |
| | | | 514/554 |
| 2009/0252796 A1 * | 10/2009 | Mazed | .................. A61K 36/02 |
| | | | 424/484 |
| 2010/0021533 A1 | 1/2010 | Mazed et al. | |
| 2011/0159118 A1 | 6/2011 | Patell | |

FOREIGN PATENT DOCUMENTS

| | | |
|---|---|---|
| EP | 1674106 B1 | 9/2011 |
| KR | 20040052398 A * | 6/2004 |
| WO | 9833494 A1 | 8/1998 |
| WO | 2006061676 A2 | 6/2006 |
| WO | 2010121320 A1 | 10/2010 |

OTHER PUBLICATIONS

Yadav, Mukesh et al, Complementary and Comparative Study on Hypoglycemic and Antihyperglycemic Activity of Various Extracts of *Eugenia jambolana* Seed, *Momordica charantia* Fruits, *Gymnema sylvestre*, and *Trigonella foenum graecum* Seeds in Rats, Applied Biochemistry and Biotechnology, vol. 160, No. 8, Apr. 2010, pp. 2388-2400.

Kochhar, Anita et al., Effect of supplementation of traditional medicinal plants on blood glucose in non-insulin-dependent diabetics: A pilot study, Journal of Medicinal Food, vol. 8, No. 4, Jan. 2005, pp. 545-549.

Rai, Amita et al., Interaction of herbs and glibenclamide: a review, ISRN Pharmacology, vol. 2012, 659478, Jul. 15, 2012 (Jul. 15, 2012), 5 pages.

Bailey, Clifford J. et al., Traditional Plant Medicines as Treatments for Diabetes, Diabetes Care, vol. 12, No. 8, Sep. 1989, pp. 553-564.

Said, Omar et al., Maintaining a Physiological Blood Glucose Level with Glucolevel, A Combination of Four Anti-Diabetes Plants Used in the Traditional Arab Herbal Medicine, eCAM, 2008:5 (4), pp. 421-428.

Dieye, A.M. et al., Medicinal plants and the treatment of diabetes in Senegal: Survey with patients, Fundamental & Clinical Pharmacology, vol. 22, Apr. 2008, pp. 211-216.

* cited by examiner

*Primary Examiner* — Michael Barker
(74) *Attorney, Agent, or Firm* — The Webb Law Firm

(57) ABSTRACT

The present invention relates to a composition a maximum of six, in particular a maximum of five or four different plant extracts for use in the prevention and/or treatment of diabetes type II or type 1. At least one plant extract has antioxidative properties and/or antioxidant enzyme inducing properties; at least one plant extract has anti-inflammatory properties; at least one plant extract has immune modulating properties; and at least one plant extract has neuronal hormone modulating properties.

15 Claims, No Drawings

COMPOSITION FOR USE AS A MEDICINE OR DIETETIC FOOD IN THE PREVENTION AND/OR TREATMENT OF DIABETES AND DIABETES ASSOCIATED DISEASES

CROSS-REFERENCE TO RELATED APPLICATIONS

This application is the United States national phase of International Application No. PCT/EP2013/070260 filed Sep. 27, 2013, and claims priority to European Patent Application No. 12186698.2 filed Sep. 28, 2012, the disclosures of which are hereby incorporated in their entirety by reference.

BACKGROUND OF THE INVENTION

Field of the Invention

The invention relates to a composition for use as medicine or dietetic food in the prevention and/or treatment of diabetes.

Description of Related Art

Diabetes mellitus is a metabolic disorder causing serious health problem all over the world. A number of associated diseases follow at a later stage. More and more people are affected by diabetes. Diabetes without proper treatments can cause serious complications including cardiovascular disease, diabetic nephropathy, diabetic retinopathy (retinal damage), diabetic neuropathy and even coma and death.

Two main types of diabetes usually occur, the type 1 or insulin dependent diabetes mellitus (IDDM), is caused by immune mediated destruction of insulin producing beta cells and type 2 or non-insulin dependent diabetes mellitus (NIDDM) results from insulin resistance, a condition in which cells fail to use insulin properly, with an absolute insulin deficiency at a later stage. Gestational diabetes, which is also a form of type 2 diabetes, occurs when pregnant women without a previous diagnosis of diabetes develop a high blood glucose level. It may precede development of type 2 DM. There are few other but seldom encountered forms of diabetes mellitus including congenital diabetes, cystic fibrosis-related diabetes, steroid diabetes and several forms of monogenic diabetes. Type 2 Diabetes is prone to be hereditary as offspring of diabetic parents are likely to develop diabetes in some stage of life.

Among all types of diabetes type 2 diabetes is most prevalent. Around 80% of diabetes cases are of type 2 and rest are mostly of type 1. The global burden of type 2 diabetes mellitus (T2DM) is currently 366 million which is predicted to increase to 552 million in 2030;

Type 2 Diabetes Mellitus is a non-autoimmune, complex, heterogeneous and polygenic metabolic disease condition in which the body produces enough insulin (at least in early stage) but it is inactive. However with progress of disease body fails to produce enough insulin at a later stage. All forms of diabetes have been treatable since insulin became available in 1921. Type 2 diabetes can be temporarily controlled with medications. Both types 1 and 2 are chronic conditions that cannot be cured.

A common approach for controlling type 2 diabetes is the administration of blood sugar lowering (hypoglycemic) agents such as biguanides like metformin or sulfonyl ureas like glibenclamid and glimepiride. However, oral hypoglycemic drugs alone or in combination are not able to achieve glycemic control permanently. As a result, as the disease progresses, physicians prescribe insulin to attenuate blood sugar. Maintaining a normal blood sugar level is the primary objective of diabetes treatment. Blood sugar lowering agents fail to maintain blood sugar level of diabetes patients in long run. Hence, though blood sugar lowering agents are essential for controlling diabetes, blood sugar lowering agents alone are not sufficient for controlling diabetes permanently.

Thus, at present there is no composition available which allows a control of the blood sugar level in a permanent way although several different approaches are under investigation.

SUMMARY OF THE INVENTION

It is therefore an object of the present invention to provide an alternative composition which can effectively maintain the blood sugar level and control diabetes for a longer period of time.

This object has been solved by providing a composition having the features as described herein.

Accordingly, a composition is provided comprising a maximum of six in particular a maximum of five or four different plant extracts for use in the prevention and/or treatment of diabetes type 2 wherein
- at least one plant extract has antioxidative properties and/or antioxidant enzyme inducing properties;
- at least one plant extract has anti-inflammatory properties;
- at least one plant extract has immune modulating properties; and
- at least one plant extract has neuronal hormone modulating properties.

The inventive composition comprises different components which are able to influence a number of different disorders typically associated with diabetes.

In the context of the present invention a plant extract is to be understood as an extract from a plant part, such as leaves, root, areal part, fruits, seeds of the fruit, fruit peel, bark or whole plant, depending upon the nature of compound desired to be obtained.

The present composition can induce production of endogen antioxidant enzymes in addition to providing powerful antioxidants to combat free radicals. This is expected to reduce oxidative stress in pancreatic islets so that beta-cell destruction may be restricted. Additionally present composition can reduce inflammation in several organs including pancreas caused by high rate of free radical attack and modulate immune system disorder typically associated with type 1 and possibly with type 2 diabetes. Last but not least present composition can modulate anomalies in neuronal hormone activity, thought to be associated with diabetes.

During research on anti-diabetic products, in particular natural anti-diabetic products, it was noticed by present inventor that for instance natural products having completely different structures and pharmacological activities exhibit positive effects on diabetes. This led to the finding of the deficiency in the present diabetes treatment and to conceive a formulation for diabetes treatment which stabilizes and improves the condition.

A further object of the present invention was to provide a composition (comprising plant extracts for the complete treatment of different disorders of diabetes) with possibility of quality control according to ICH guidelines. Strict quality control is particularly emphasized for herbal products, because the composition of a plant extract is not a fixed composition and can vary largely depending upon region to region, season to season and different varieties of the same plant and can have immense effect on efficacy.

According to the invention this object is being solved by providing a composition comprising a maximum of six plant extracts, in particular a maximum of five or four plant extracts having specific pharmacological properties. The limited number of ingredients allows for a complete method development for quality control, method validation according to ICH guidelines and stability study of the product. When these aspects lack in a product, its efficacy cannot be guaranteed. This is particularly true for herbal products because it is well known that chemical constituents of herbal ingredients show geographical and seasonal variation in presence or absence of many constituents as well as variation in their quantity. As per rule both medicine as well as dietetic formulations for diabetics or balanced diet, (such as described in this invention) are special product categories which are to be consumed under close observation by a physician and for which maintenance of quality control is essential.

Diabetes is known to be associated with high oxidative stress. Reactive oxygen species (ROS) produced in excessive amount, are responsible for high oxidative stress in biological system. Endogen antioxidants, like superoxide dismutase and glutathione, clear ROS produced during metabolic process in mitochondria. If this regulated clearance of ROS is hampered due to some metabolic disorder, high oxidative stress may persist leading to mitochondrial dysfunction and beta-cell apoptosis, as seen in type 2 diabetes mellitus.

Malondialdehyde (MDA) is a well known marker for oxidative stress. Malondialdehyde level was found to be significantly higher in plasma and urine of diabetic patients compared to normal subjects, showing high oxidative stress in diabetics. These observations evidently prompted many investigations to show the effect of vitamins (as anti-oxidant) in diabetes control. However, results revealed that vitamins alone have no effect on diabetes control.

According to the present invention the reasons for high oxidative stress in diabetes and diabetes associated diseases are (i) low production of endogen antioxidant enzymes on one hand and (ii) increased production of free radicals due to high blood glucose level on the other.

Thus, high oxidative stress prevails in diabetes. It is postulated that high oxidative stress in pancreatic islets leads to gradual apoptosis of beta cells, which in turn causes reduction in insulin production leading to uncontrolled diabetes. At this stage blood sugar lowering agents alone are no more able to achieve adequate glycemic control. Hence, it was realized that low levels of endogenous antioxidants in pancreatic mitochondria may be an important reason for beta cell apoptosis leading to uncontrolled diabetes and only adequate level of endogen antioxidant enzymes capable of destroying free radicals in mitochondria in-situ can reduce oxidative stress effectively. Thus diabetes type 2 should be treated with constituents capable of induction of antioxidant enzyme on one hand and blood sugar lowering agents on the other.

The present composition is now able to manage these two aspects by providing i) ingredients or substances capable of inducing antioxidant enzymes and (ii) strong antioxidants of plant origin to capture free radicals in outer mitochondrial system, respectively. Additional features of the formulation are use of anti-inflammatory ingredients, immune-modulators and neuronal-hormone modulator as described in detail further below.

As described above the present composition comprises at least one plant extract having antioxidative properties and anti-oxidant enzyme inducing properties. This is expected to reduce oxidative stress in pancreatic islets so that beta-cell destruction may be restricted.

Thus, at least one plant extract or substance should be capable of anti oxidant enzyme induction in order to elevate endogen antioxidant enzyme levels in important organs like pancreas and heart causing in-situ destruction of free radicals, thereby lowering the oxidative stress, which is in particular responsible for apoptosis of cells and especially beta cells in pancreas.

Furthermore, the present composition comprises at least one plant extract for reducing inflammation, particularly inflammation associated with apoptosis of beta cells in pancreas, which in turn may facilitate the generation of new beta cells.

The present composition also comprises at least one plant extract having immune modulating properties influences the immune system as the immune system might play an important role in etiology of type 2 diabetes as it does in case of type I diabetes;

Finally, the present composition comprises at least one plant extract having neuronal hormone modulating properties that attenuates the neuronal hormones, since diabetes is known to be associated with changes in the hypothalamic-pituitary-adrenal (HPA) axis.

The combined effect of above measures causes an overall reduction of oxidative stress including in pancreas leading to regeneration and stabilization of beta cells, which in turn control and restrict diabetes effectively.

The present composition is characterized by a synergetic effect of these different plant extracts and their respective ingredients or ingredients that is responsible for durable control of blood sugar level and for stopping the progress of diabetes.

As mentioned previously the present composition is used in the prevention and/or treatment of diabetes, in particular diabetes type 2.

Hypoglycemic agents have been standard therapy of diabetes type 2 for a long time. Present invention discovers for the first time, that the standard therapy with hypoglycemic agents can be supplemented with present composition for an effective and permanent treatment of diabetes type 2.

By definition, hypoglycemic agents are those medicines that help to transport blood sugar into the cells. They act upon the mechanism of glucose transportation from blood into the cells. The ingredients of the present invention does not act upon glucose transportation, therefore, they are not hypoglycemic agents. It is of advantage to treat diabetes with hypoglycemic agents since high blood sugar level must come down as soon as possible. High level of blood sugar causes two folds damage to the organs, first by glucosylation of proteins and secondly by increasing the free radical production. However, as mentioned before, hypoglycemic agents alone cannot stop the progress of diabetes, which was the reason for the research leading to the present invention.

Although the present composition (like hypoglycemic agents) also lowers blood sugar level and other diabetes parameters (s. Clinical trial), it takes time to observe these effects, because the actions of composition take place in molecular level. Hence, it is of an advantage to add hypoglycemic agents (either synthetic or of plant origin) to the present composition to bring the blood sugar quickly down.

According to present invention it is preferred to treat diabetes with hypoglycemic agents combined with the present composition, since present composition treats the root cause of diabetes type 2 and stabilizes the blood sugar level for long duration.

In a preferred embodiment the present composition is used alone for prevention or control of blood sugar level in early stage of diabetes. The composition may be used alone as prophylactic or as treatment for type 2 diabetes in early stage. For diabetes in advanced stage it may be used in combination with oral hypoglycemic agents of natural or synthetic origin.

In another preferred embodiment the present composition is used in a complementary treatment of diabetes type 2 together with at least one hypoglycemic agent, such as an oral hypoglycemic agent, or a combination of two hypoglycemic agents, such as in cases of patients in advanced stages of diabetes and showing very high fastening blood sugar (FBS) and HbA1c values.

Thus, it is preferred to use the present composition in combination with at least one hypoglycemic agent, which may be of plant or synthetic origin, for a full therapeutic effect, except in case of early stage of diabetes. The hypoglycemic agent may be a part of the composition or a separate product. It is however to be understood that the hypoglycemic agent is added as an extra compound to the present composition comprising a maximum of plant extracts with the described properties.

A suitable hypoglycemic agent may be selected from a group comprising synthetic substances such as biguanides like metformin or sulfonyl ureas like glibenclamid and glimepiride or natural substances originating from plant extracts such as *Azadirachta indica* (neem) extract, *Eugenia jambolana* (jamun) seed extract, *Gymnema sylvestre* Extract, *Momordica charantia* (Karela) extract, *coccinia indica* extract or a combination thereof.

For instance, in a clinical trial conducted on diabetes type 2 patients having high fasting blood sugar values and receiving metformin and glimepiride for at least three months (but not responding to this therapy), were additionally prescribed one capsules of the present composition twice daily. The effect of the present composition was manifested by gradual reduction of blood sugar level as shown in detail in the example section. In this example the present composition was used as complimentary treatment of advanced stage of diabetes type 2 where hypoglycemic agents were separate products.

It is particularly mentioned here, that the existing therapy with oral hypoglycemic agents should not be interrupted, as it may lead to glycemic shock. With patients already receiving oral hypoglycemic agents, therapy is preferably complemented with present composition and the dose of hypoglycemic agent may be reduced gradually little by little when fasting blood sugar value falls down below 90 mg/dl.

For newly diagnosed diabetes type 2 patients showing advanced stage of diabetes type 2 (that means having a high blood sugar level of about 200 mg/dl) the oral hypoglycaemic agent in a usual dose (that is the dose generally applied in advanced stage of diabetes) together with present composition should be preferred. In such a case the dose of hypoglycaemic agent should be chosen according to physician's preference and independent of the dose of present composition.

Present composition should be given additionally to the hypoglycaemic medicine in dose of two capsules daily. One capsule may contain 100 to 500 mg, preferably 200 to 400 mg, in particular preferably 350 mg of the present composition.

If hypoglycemic agent and the present composition are administered together then fasting blood sugar and HbA1C values should be watched regularly. When these values tend to approach below normal (ca. 90 mg/dl for fasting blood sugar and 6% for HbA1C) values the dose of hypoglycaemic agent should be reduced in small steps. Reduction of hypoglycaemic agent may cause temporary rise in FBS, which comes down again within few days.

In a preferred embodiment the present composition is used as a dietary formulation for treatment of diabetes type 2, for instance in combination with oral hypoglycemic agents like metformin. For instance, as described in detail also in the example section, in a single arm, GCP controlled, exploratory clinical trial conducted on diabetes type 2 patients who were being treated with oral hypoglycemic agents for at least one year and receiving a stable dose of combination of metformin and glimepiride without any improvement, were additionally prescribed one capsules twice daily of present composition. The efficacy of the present composition was exhibited by gradual reduction of blood sugar level and HbA1C value. In some cases the fasting blood sugar level reached under normal value and there was an incident of hypoglycemia. This also indicates that the dose of hypoglycemic agents may be required to be reduced when fasting blood sugar level tends to reach below normal (ca. 80-90 mg/dl) value. The reason for reducing hypoglycemic agent and not the composition is simply that hypoglycemic agents reduce the symptom of diabetes (high blood sugar level) whereas the invention composition counteracted the underlying causes.

Hence, when required, the dose of composition should preferably be kept steady, while the dose of hypoglycemic agent should be adjusted according to the rate of improvement as indicated by decreasing values of FBS and HbA1C.

Depending upon degree of inner damage, diabetes patients may need a minimum dose of blood sugar lowering agent in addition to the composition to maintain the stable condition. The composition alone does not cause hypoglycemia, because no blood sugar lowering agent has been included in this composition.

Though both blood sugar lowering agents and the present formulation ultimately show their beneficial effect through lowering of blood sugar, the difference lies in the mechanism of action. The so called hypoglycemic agents directly transfer the sugar from blood into the cells either by insulin sensitization like metformin and *Eugenia jambolana* (inactive insulin binds again to the receptors so that glut 4 can come to the cell surface and transport sugar into the cells) or by squeezing some insulin from remaining beta cells, like sulphonyl ureas and *Gymnema sylvestre*, or directly act as Glut 4 and transport sugar to the cells, like *Momordica charantia* and *coccinia indica*.

Whereas the hypoglycemic agents bring temporary improvement as long as surviving beta cells are able to produce some minimum quantity of insulin, components of the formulation help to rehabilitate the normal insulin production and function, leading to permanent glycemic control and stabilization.

If the diabetes is still in the early stage (that means the blood sugar level is not higher than 120 mg/dl) then the present composition can be administered alone without the hypoglycemic agent. In such case two capsules containing the present composition are administered to the patient. Furthermore, for newly diagnosed diabetes type 2 patients showing early stage of diabetes, the present composition in combination with a general dietary precautions and physical exercise may stop the outbreak of diabetes.

In another embodiment the present composition is used in the prevention and/or treatment of secondary diseases associated with diabetes and/or high oxidative stress, in particular cardiovascular diseases, hyperlipidemia, retinopathy or nephropathy.

In another embodiment it is possible to add at least one synthetic ingredient to the present composition comprising a maximum of five plant extracts.

Such a synthetic ingredient may be selected as follows:
at least one synthetic ingredient having antioxidative properties and/or anti-oxidant enzyme inducing properties is selected from a group comprising Vitamin C, Vitamin E, indole-3-carbinol, glutathione and others;
at least one synthetic ingredient having anti-inflammatory properties is selected from a group comprising non-steroidal antiphlogistics such as acetylsalicylic acid, benzydaminhydrochlorid, ibuprofen, naproxen, ketoprofen, or glucocorticoides such as hydrocortison, prednisolon, fluticason and others;
at least one synthetic ingredient having immune modulating properties is selected from a group comprising cytokines such as interferones or interleukines; growth factors; proteins, immune-suppressive agents such as 6-mercaptopurine, 5-fugoruratsil or azathioprine, antibiotics such as obtained from Actinomycetes or others; and
at least one synthetic ingredient having neuronal hormone modulating properties is selected from a group comprising Vitamin D and related compounds.

It is particular preferred if the plant extract capable of inducing antioxidant enzymes as well as having antioxidant properties originate or are isolated from a group of plants comprising *Vitis* species, like *Vitis vinefera*, *Phyllanthus* species, like *Phyllanthus emblica* (Indian gooseberry), *Aronia* species, like *Aronia melanocarpa* (chokeberry) *Pterocarpus* species, like *Pterocarpus marsupium*, *Swertia* species, like *Swertia chirayta*, *Mangifera* species, like *Mangifera indica*, *Cinnamomun* species, like *Cinnamomum verum*, *Garcinia* species, like *Garcinia mangostana*, *Camellia* sp., like *Camellia sinensis*, *Vaccinium* species, like *Vaccinium myrtillus* L. or *Vaccinium oxycoccos* and *Punica granatum*.

In a preferred embodiment of the present composition the at least one plant extract having antioxidative properties and/or antioxidant enzyme inducing properties is selected from a group comprising bilberry (*Vaccinium myrtillus* L.) extract, cranberry (*Vaccinium oxycoccos*) extract, grape (*Vitis vinifera*) seed extract, *Phyllanthus emblica* (Indian gooseberry) extract, *Aronia melanocarpa* (chokeberry) extract, *Pterocarpus marsupium* extract, *Swertia chirayta*, *Mangifera indica* bark, Cinnamon bark, *Garcenia mangostana* extract, green tea (*Camelia sinensis*) leaves and *Punica granatum* whole fruit or peel extracts.

The antioxidative properties of above plant extracts (i.e. high ORAC value) is in particular due to plant polyphenols such as flavonids, ellagitannins, xanthones, tannins and anthocyanins.

In a yet further embodiment the at least one plant extract having anti-inflammatory properties is selected from a group of plants comprising *Curcuma* species, like *Curcuma longa* (turmeric), *Salix* species (willow), *Garcinia* species, like *Garcinia mangostana*, *Aloe* species, like *Aloe vera* and *Swertia* species, like *Swertia chitayta*.

Thus, in a preferred embodiment the at least plant extract having anti-inflammatory properties is selected from plant extracts such a *Curcuma longa* (turmeric) extract, willow (*Salix*) bark, *Aloe vera* extract, *Garcenia mangostana* extract and *Swertia chirayta* extract.

It is particular preferred that at least one plant extract having anti-inflammatory properties is selected as *Curcuma longa* (turmeric) extract, because *Curcuma longa* has not only excellent anti-inflammatory properties, but also exhibits antioxidant, hepatoprotective, anti-bacterial and immunostimulatory effect.

The anti-inflammatory properties of said plant extracts is in particular due to the action of plant antiphlogistics.

It is yet further preferred if the at least one plant extract having immune modulating properties is selected from a group comprising plant polysaccharides, in particular galactomannans, acemannans, arabinoglucans, glucans and mixed polysacharides.

It is in particular preferred if the plant extracts having immune modulating properteis originate or are isolated from a group of plants comprising *Trigonella* species, like *Trigonella foenum-graecum* (fenugreek), *Tinospora* species, like *Tinospora cordifolia*, *Senna* species, like *Cassia auriculata* and *Echinacea* species.

Thus it is preferred if the at least one plant extrac having immune modulating properties is selected from a group comprising *Trigonella foenum-graecum* (fenugreek) seed extract, *Tinospora cordifolia* extract, *Cassia auriculata* extract and *echinacea* extract.

Plant based Immuno-modulating agents have been reported to act primarily on cellular rather than humoral immune responses and to restore the immuno-competency of impaired hosts without hyperstimulating the normals. It augments macrophage chemotaxis, phagocytosis and promotes interaction with other immunoregulatory lymphoid cells.

The immune modulating properties of the selected plant extracts are mainly due to the action of different plant polysaccharides, in particular galactomannans, acemannans, arabinoglucans, glucans and mixed polysacharides.

In another variant of the present composition the at least one plant extract having neuronal hormone modulating properties originate from a group of plants comprising *Trigonella* species, like *Trigonella foenum-graecum* (fenugreek), *Whitania* species, like *Withania somniflora* (winter cherry) and *ginseng* species, like *Panax gingseng*.

Thus, in a preferred embodiment the at least one plant extract having neuronal hormone modulating properties is selected from a group comprising *Trigonella foenum-graecum* (fenugreek) seed extract, *Withenia somniflora* (winter cherry) extract and *Panax gingseng* extract.

The neuronal hormone modulating properties of the selected plant extracts is mainly due to the action of plant Steroid, in particular steroid or steroidal saponins, or corresponding aglycons, in particular withanolides, gingseng saponins and furo- and spirostanol saponins.

Specific compositions for the use in maintaining and/or reducing the blood sugar level, in particular in case of diabetes as of type 2 may comprise the following ingredients:

a) *Vitis vinifera* (grape) seed extract, *Phyllanthus emblica* (Indian gooseberry) extract, *Curcuma longa* (turmeric) extract and *Trigonella foenum-graecum* (fenugreek) seed extract;

b) *Phyllanthus emblica* (Indian gooseberry) extract, *Aronia melanocarpa* (chokeberry) extract, *Curcuma longa* (turmeric) extract, *Tinospora cordfolia* extract and *Withenia somniflora* (winter cherry) extract;

c) *Phyllanthus emblica* (Indian gooseberry) extract, *Garcenia mangostana* hull extract, *Curcuma longa* (turmeric) extract, and *Trigonella foenum-graecum* (fenugreek) seed extract;

d) *Phyllanthus emblica* (Indian gooseberry) extract, *Pterocarpus marsupium* extract, *Curcuma longa* (turmeric) extract, *Tinospora cordfolia* extract and *Swertia chirayta* extract;

e) *Phyllanthus emblica* (Indian gooseberry) extract, *Mangifera indica* bark extract, *Curcuma longa* (turmeric) extract, *Tinospora cordfolia* extract and *Swertia chirayta* extract;

f) *Phyllanthus emblica* (Indian gooseberry) extract, *Pterocarpus marsupium* extract, *Curcuma longa* (turmeric) extract, *Tinospora cordfolia* extract and *Panax gingseng* extract;

g) *Phyllanthus emblica* (Indian gooseberry) extract, *Curcuma longa* (turmeric) extract, *echinacea* extract and *Panax gingseng* extract, h) *Phyllanthus emblica* (Indian gooseberry) extract, *Aronia melanocarpa* (chokeberry) extract, *Curcuma longa* (turmeric) extract, and *Trigonella foenum-graecum* (fenugreek) seed extract;

i) *Phyllanthus emblica* (Indian gooseberry) extract, *Pterocarpus marsupium* extract, *Curcuma longa* (turmeric) extract, *Tinospora cordfolia* extract and *Withenia somniflora* extract;

j) *Phyllanthus emblica* (Indian gooseberry) extract, *Vitis vinifera* (grape) seed extract, acetyl salicylic acid, *Tinospora cordfolia* extract and *Withenia somniflora* extract;

k) *Phyllanthus emblica* (Indian gooseberry) extract, *Swertia chitayta*, *Curcuma longa* (turmeric) extract and *Tinospora cordifolia* extract l) *Vitis vinifera* (grape) seed extract, *Curcuma longa* (turmeric) extract, Vitamin D3 and *Trigonella foenum-graecum* (fenugreek) seed extract;

m) *Phyllanthus emblica* (Indian gooseberry) extract, *Pterocarpus marsupium* extract, *Curcuma longa* (turmeric) extract, *Tinospora cordfolia* extract and *Garcinia mangosta* n) *Phyllanthus emblica* (Indian gooseberry) extract, *Swertia chitayta*, *Curcuma longa* (turmeric) extract, *Tinospora cordifolia* extract and *Eugenia jambolana* seed extract; or o) *Phyllanthus emblica* (Indian gooseberry) extract, *Pterocarpus marsupium* extract, *Curcuma longa* (turmeric) extract, *Panax gingseng* extract and *Coccinia indica* extract p) *Phyllanthus emblica* (Indian gooseberry) extract, *Pterocarpus marsupium* extract, *Curcuma longa* (turmeric) extract, *Swertia chirayta* and *Azadirachta* extract Examples (n), (o) and (p) embody compositions, where a blood sugar lowering (hypoglycemic) plant extract is incorporated in the formulation. This type of formulation may be particularly helpful for treating severe diabetes not responding to the treatment with oral hypoglycemic agents alone. The existing hypoglycemic therapeutic agents should not be abruptly discontinued, instead composition of type (n)-(p) should be additionally taken. In case of severe diabetes it may take longer time to achieve normal or near to normal blood sugar value.

In the context of the present disclosure it is also to be understood that the properties of the present composition do not necessarily have to be assigned to one single plant extract. It may also be possible that one plant extract provides for more than one property, such as two properties as claimed. This may be the case if an ingredient has similar biochemical or therapeutic functionalities. Therefore, the present composition may also comprise less than five or four plant extracts, such as three or two plant extracts. However, the maximum number of plant extracts in the composition never exceeds six, preferably five, most preferably four plant extracts.

Thus, in a preferred case the present composition comprises four, five or six different plant extracts having one of the specifically required properties as defined above.

The present composition may also comprise one synthetic ingredient and three, four, five or six different plant extracts. Any conceivable combination is hereby possible.

However, it is also possible that one plant extract used in the present composition may have for instance immune modulating properties and also neuronal hormone modulating properties. Thus, in such a case one plant extract may be used for more than one purpose, and the present composition may thus comprise in total less than four, five or six plant extracts, however still comprising the properties as required by the present composition.

Typically plant extracts may comprise multiple ingredients or agents which have different properties and thus would be applicable in more than only one of the above listed groups of agents. For instance, a plant extract may contain agents which confer the plant extract with immune modulating properties and neuronal hormone modulating properties, such as fenugreek extracts as shown further below.

The present composition preferably comprises:
a) 20 to 200 mg, preferably 50 to 150 mg, in particular preferably 70 to 100 mg of the least one plant extract having antioxidative properties and/or anti-oxidant enzyme inducing properties in particular endogen antioxidant enzyme inducing properties;
b) 20 to 200 mg, preferably 50 to 150 mg, in particular preferably 70 to 120 mg, of the least one plant extract having anti-inflammatory properties;
c) 20 to 200 mg, preferably 50 to 150 mg, in particular preferably 70 to 100 mg of the at least one plant extract having immune modulating properties, and
d) 20 to 200 mg, preferably 50 to 150 mg, in particular preferably 70 to 100 mg at least one plant extract having neuronal hormone modulating properties.

It is of course to be understood that the amounts provided above depend on the bioavailability of the ingredients or constituents as well as on the amount of co-existing active substances, particularly when using an ingredient of plant origin and may therefore vary in the mentioned ranges.

For instance, when using herbal products, a single ingredient (plant extract), that contains components having more than one desired properties, has to be used in higher amount in order to avail adequate amount of each type of components. For example in case of fenugreek seed extract, the amount of extract used in the composition is generally higher than other ingredients, because adequate amount of both galactomanans and steroidal saponins have to be included.

As mentioned previously a plant extract is to be understood as an extract from a plant part, such as leaves, root, areal part, fruits, seeds of the fruit, fruit peel, bark or whole plant, depending upon the nature of compound desired to be obtained.

A plant extract means extract from a plant part, such as leaves, root, areal part, fruits, seeds of the fruit, fruit peel, bark or whole plant, depending upon the nature of compound desired to be obtained. Water, organic solvents or a mixture of the two can be used for extraction, again depending upon the nature of compounds desired to be extracted. This point is illustrated in following examples in more detail For example, in case of *Garcenia mangostana* hull the compounds desired to be extracted are xanthones, which are a class of compound more soluble in methanol or ethanol rather than water. Hence alcohol such ethanol should be used for extraction instead of water or water-alcohol mixture. Other solvents like methanol can also be used but care should be taken to completely remove the traces of the solvents from the extract because of higher toxicity of methanol.

In case of green tea on the other hand, the water soluble catechins like gallocatechins, epigallocatechin, epigallocatechin gallate, epicatechin gallate, gallate glycosides etc. are the desired compound, hence water should be preferably used for extraction.

*Withenia somniflora* contains with enolides as main active principle possessing neuro-hormonal modulating properties, which are more alcohol soluble rather than water soluble. The plant also contains water soluble active polysaccharides which have immune modulating properties. Hence, in case both activities are of important in a formulation, a water-alcohol, like 70% water-alcohol extract should be used.

Thus, selection of a proper plant part, extraction solvent, extraction process and process of drying the extract all play crucial roles in the bio-activity of a plant extract. It is therefore important to mention here, that commercially available plant extracts are not always suitable for using as ingredient in a herbal product particularly in the present composition. Care should be taken to use ingredients of proper quality and a quality control parameter should be developed and applied to maintain the same quality for all batches of production.

The present composition may be used either as a pharmaceutical composition in the prevention and/or treatment of high sugar levels such as in case of diabetes or may also be used as a dietetic food as for instance as a supplementary for maintaining or stabilizing the blood sugar level, or for preventing and/or treating secondary diseases associated with diabetes and/or with high oxidative stress, in particular cardiovascular diseases, hyperlipidemia, retinopathy or nephropathy.

As previously described the present composition such as in form of herbal medicine is suitable for restricting diabetes alone or in addition to one of the conventional used hypoglycemic agents. Thus, the present composition is used for maintaining and/or reducing the blood sugar level in diabetes patients or even for prevention the outbreak of diabetes in a way of prophylaxis.

The present composition may also be useable in a method for preventing and/or treating symptoms, conditions or disorders associated with diabetes such as diabetes type 2, preventing and treating cardiovascular disorder, preventing and treating hyperlipidemea. According to this method the present composition is administered alone (as prevention) or together with another hypoglycemic agent at least once, preferably at least twice a day.

DETAILED DESCRIPTION OF THE INVENTION

Further details of the invention are explained in more detail by the means of various exemplary embodiments.

EXAMPLE

A composition as dietetic food for diabetics comprising *Vitis vinifera* (grape) seed water extract (80 mg), *Phyllanthus emblica* (Indian gooseberry) hydro-alcoholic extract (90 mg), *Curcuma longa* (turmeric, 80 mg) alcoholic extract and *Trigonella foenum-graecum* (fenugreek) seed hydro-alcohol extract (110 mg) was used for demonstrating the efficacy in a clinical study.

The extraction process for individual ingredients was selected according to the nature of active compound present in the plants. Therefore, commercially available extracts were not used in the particular composition mentioned above. *Vitis vinifera* (grape) seed was extracted with water in order to extract the monomers and dimmers of proanthocyanidins of grape seed preferably. *Phyllanthus emblica* was extracted with a mixture of water and alcohol for extracting ellagitannins as well as their glycosides. *Curcuma longa* on the other hand contains curcumin and dihydro curcumins as active constituents, and they are more soluble in organic solvent and therefore alcohol was used for extraction. *Trigonella foenum-graecum* (fenugreek) contains water soluble polysaccharides as well as steroidal sapogenins and genins as active components, which are more alcohol soluble and hence, mixture of water and alcohol was used for extraction.

In a single arm, GCP controlled clinical study effect of the above dietetic composition was studied on 40 diabetes patients. Diabetes type 2 patients, who were under treatment for diabetes for more than one year and receiving a combination therapy of metformin and glimepiride were included in the study. In spite of combination therapy most of the patients were showing poor glycemic control as evident by fasting blood sugar and HbA1C values. Subjects were receiving mostly the combination of metformin and glimepiride for at least one year and were consuming the same dose for at least three months prior to study begin. They were given the above composition (one capsule, twice daily) in addition to the hypoglycemic agents. All concomitant drugs taken for other associated diseases including hypertension and hyperlipidemiae were continued as before.

Subjects were instructed to avoid any change in general diet, life style or medicine intake. No other herbal drug except the above composition was permitted. Aim of the study was to observe the effect of the present dietetic composition (taken additionally to the oral hypoglycemic agents) on blood sugar level and HbA1C value and on lipid parameter. The primary end points were fall in fasting blood sugar, and HbA1C values compared to starting point. Results of the study are presented in the following table 1.

The results of this study demonstrated the positive effect of the complementary treatment with the herbal composition along with hypoglycemic agents compared to hypoglycemic agent alone (initial values). Moreover, the almost same average fasting blood sugar (FBS) values of day 42 and day 63 is because of a number of patients who forgot to take the herbal composition on several days during this period. As a result their FBS were again higher than before so that the average value went high. Thus skipping a dose caused reversal of positive effect.

The treatment should be conducted under medical supervision since considerable lowering of blood sugar values were observed in many cases, indicating the need for reducing the amount of hypoglycemic agent.

TABLE 1

Effect of dietetic food on diabetes Type 2: Changes in diabetic parameters within 12 weeks of treatment period

| Description | Parameter | Study beginn (Day 0=) | Middle of study (Day 42) | End of study (Day 84) |
|---|---|---|---|---|
| Subjects with moderate diabetes FBS < 150 mg/dl | FBS (mg/dl) Average value (n = 12) | 128 | 117 | 112 |
| Subjects with advanced diabetes FBS > 150 mg/dl | FBS (mg/dl) Average value (n = 28) | 190 | 139 | 128 |
| HbA1C | Average (%) (n = 40) | 8.9 | 8.1 | 7.6 |
| Triglycerid | Durchschnittswert (mg/dl) (n = 40) | 162 | — | 146 |

The results of this study demonstrated the positive effect of the complementary treatment with the herbal composition along with hypoglycemic agents over hypoglycemic agent alone (initial values).

The invention claimed is:

1. A method of decreasing high oxidative stress in pancreas of a patient with type II diabetes, reducing beta cell apoptosis, and facilitating regeneration of beta cells, comprising administering to an individual in need thereof a composition comprising 160 mg of *Vitis vinifera* (grape) seed extract, 180 mg of *Phyllanthus emblica* (Indian gooseberry) extract, 160 mg of *Curcuma longa* (turmeric) extract, and 220 mg of *Trigonella foenum-graecum* (fenugreek) seed extract daily, thereby restoring insulin production and reducing and stabilizing blood sugar in the patient.

2. The method according to claim 1, wherein the individual has advanced stage diabetes type II, and wherein the composition is administered with at least one hypoglycaemic agent either as a component of the composition or as a separate composition, thereby providing a more rapid reduction and stabilization of blood sugar.

3. The method according to claim 2, wherein the hypoglycaemic agent is one or more plant extracts selected from the genera *Azadirachta, Eugenia, Gymnema, Momordica, Coccinia*, and combinations thereof.

4. The method according to claim 3, wherein the hypoglycaemic agent is one or more plant extracts selected from *Azadirachta indica, Eugenia jambolana, Gymnema sylvestre, Momordica charantia, Coccinia indica*, and combinations thereof.

5. The method according to claim 2, wherein the hypoglycaemic agent is a biguanide.

6. The method according to claim 2, wherein the hypoglycaemic agent is metformin.

7. The method according to claim 2, wherein the hypoglycaemic agent is a sulfonyl urea.

8. The method according to claim 2, wherein the hypoglycaemic agent is glibebclamide or glimepiride.

9. The method according to claim 2, wherein the hypoglycaemic agent is a combination of metformin and glimepiride.

10. The method according to claim 2, wherein the hypoglycaemic agent is a single or combined conventional diabetes medicine, is of plant origin, or is a combination of both.

11. The method according to claim 1, wherein the method is used in the treatment for diabetes type II in advanced stage.

12. The method according to claim 11, wherein the method is used in the treatment of a secondary disease associated with high oxidative stress found in diabetes type II in advanced stage.

13. The method according to claim 12, wherein the method is used in the treatment of a secondary disease associated with high oxidative stress found in diabetes is cardiovascular disease and hyperlipidemia.

14. The method according to claim 1, wherein the individual has early stage diabetes type II, and is being treated with one or more oral hypoglycemic medicines, wherein the composition is administered in addition to the oral hypoglycemic medicine for reducing beta cell apoptosis, restoring insulin production, and reducing and stabilizing blood sugar in the patient.

15. The method according to claim 1, wherein the individual is a diabetes type II patient who is no longer responding to treatment with oral hypoglycemic agents.

* * * * *